US010376232B2

(12) United States Patent
Ertel

(10) Patent No.: US 10,376,232 B2
(45) Date of Patent: Aug. 13, 2019

(54) METHOD AND X-RAY IMAGING DEVICE FOR AUTOMATICALLY CONTROLLING THE EXPOSURE IN X-RAY IMAGING

(71) Applicant: Siemens Healthcare GmbH, Erlangen (DE)

(72) Inventor: Dirk Ertel, Forchheim (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/092,254

(22) PCT Filed: Feb. 24, 2017

(86) PCT No.: PCT/EP2017/054287
§ 371 (c)(1),
(2) Date: Oct. 9, 2018

(87) PCT Pub. No.: WO2017/178144
PCT Pub. Date: Oct. 19, 2017

(65) Prior Publication Data
US 2019/0133543 A1 May 9, 2019

(30) Foreign Application Priority Data

Apr. 12, 2016 (DE) .................. 10 2016 206 071

(51) Int. Cl.
*A61B 6/00* (2006.01)
*H05G 1/42* (2006.01)
(52) U.S. Cl.
CPC .............. *A61B 6/542* (2013.01); *H05G 1/42* (2013.01); *A61B 6/503* (2013.01); *A61B 6/504* (2013.01)

(58) Field of Classification Search
CPC ..... A61B 6/4441; A61B 6/542; A61B 6/4225; A61B 6/548; A61B 6/503; A61B 6/504; H05G 1/42
See application file for complete search history.

(56) References Cited

U.S. PATENT DOCUMENTS 5,949,811 A    9/1999  Baba et al.
7,496,175 B2 * 2/2009  Sakaguchi ........... A61B 6/4233
                                              378/95

(Continued)

FOREIGN PATENT DOCUMENTS

CN    1912604 A    2/2007
CN    103654810 A  3/2014

(Continued)

OTHER PUBLICATIONS

German Decision to grant for German Application No. 102016206071.6 dated Aug. 7, 2018 with English translation herewith.

(Continued)

*Primary Examiner* — Chih-Cheng Kao
(74) *Attorney, Agent, or Firm* — Harness, Dickey & Pierce, P.L.C.

(57) ABSTRACT

A method is disclosed for automatically controlling the exposure in an X-ray imaging of a moving object to be irradiated. An embodiment of the method includes generating X-ray images at different times with a predeterminable pulse width of X-ray radiation; determining at least one moving image region from at least two of the generated X-ray images; determining at least one moving edge of the moving image region; selecting at least one pixel of the edge; determining the time dependence of the intensity of the pixel from the generated X-ray images; evaluating the time dependence of the intensity; and changing the pulse width in accordance with the evaluation. Alternatively, the spatial dependency of the intensity can also be evaluated (Continued)

close to the edge. Advantages of ensuring an optimum image quality and reducing negative influences of a sub-optimum parameter selection are realized.

20 Claims, 1 Drawing Sheet

(56) References Cited

U.S. PATENT DOCUMENTS

| | | |
|---|---|---|
| 2007/0030944 A1 | 2/2007 | Grasruck et al. |
| 2007/0047794 A1 | 3/2007 | Lang |
| 2008/0240355 A1* | 10/2008 | Ohishi ............... A61B 6/4441 378/98 |
| 2014/0064444 A1 | 3/2014 | Oh et al. |
| 2016/0089102 A1 | 3/2016 | Wang et al. |

FOREIGN PATENT DOCUMENTS

| | | |
|---|---|---|
| CN | 105358062 A | 2/2016 |
| DE | 102010061884 A1 | 5/2012 |
| JP | 2015134168 A | 7/2015 |

OTHER PUBLICATIONS

German Office Action for German Application No. 102016206071.6 dated Feb. 15, 2017 with English translation herewith.
International Search Report PCT/ISA/210 for International Application No. PCT/EP2017/054287 dated May 30, 2017 with English translation herewith.
Written Opinion of the International Searching Authority PCT/ISA/237 for International Application No. PCT/EP2017/054287 dated May 30, 2017 with English translation herewith.
Chinese Office Action and English translation thereof dated Apr. 28, 2019.

* cited by examiner

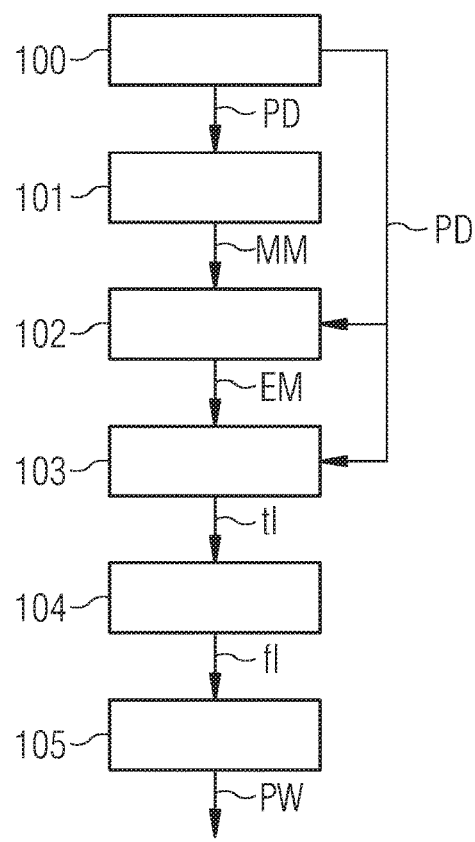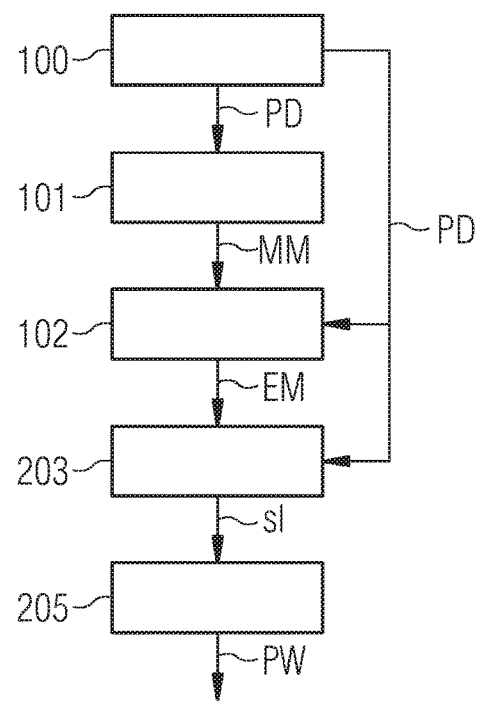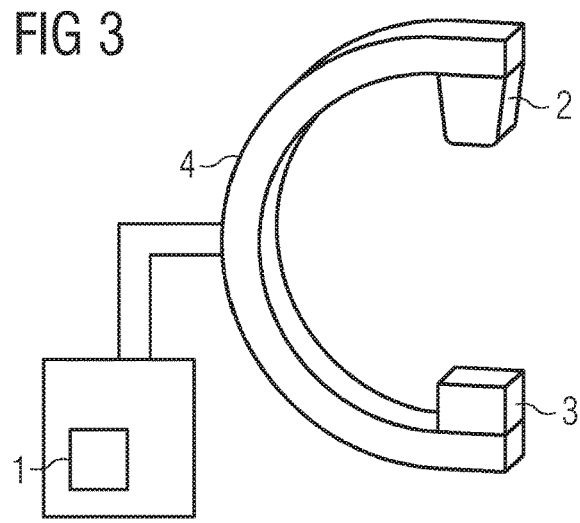

METHOD AND X-RAY IMAGING DEVICE FOR AUTOMATICALLY CONTROLLING THE EXPOSURE IN X-RAY IMAGING

PRIORITY STATEMENT

This application is the national phase under 35 U.S.C. § 371 of PCT International Application No. PCT/EP2017/054287 which has an International filing date of Feb. 24, 2017, which designated the United States of America and which claims priority to German patent application number DE 102016206071.6 filed Apr. 12, 2016, the entire contents of which are hereby incorporated herein by reference.

FIELD

Embodiments of the invention generally relate to a method and to an x-ray imaging device for automatic exposure control in x-ray imaging of objects that are moving and are to be irradiated. Embodiments of the invention also generally relate to an associated digital storage medium.

BACKGROUND

Devices for x-ray imaging feature automatic exposure control. This insures that an adequate signal strength is always present at the input of an x-ray detector. This is achieved by setting various x-ray parameters, above all through an adjustment of the tube voltage, of the tube current, of the tube pre-filter and of the pulse width of the x-ray radiation.

Thus, if the absorption behavior of the object to be examined or irradiated changes, through a change in the fluoroscopy angle for example, the aforesaid parameters are adjusted automatically, whereby a constant signal strength is guaranteed at the input of the x-ray detector.

Each change in the x-ray parameters is also associated with disadvantages however, which have a negative influence on an x-ray imaging, such as for example:
  a lower image contrast for an increased signal caused by a higher tube voltage,
  a greater x-ray focus and thus a lower spatial resolution through an increased signal caused by a higher tube current,
  a higher skin dose through an increased signal caused by a lower x-ray pre-filtering and also
  a lower time resolution through an increased signal caused by a longer pulse width of the x-ray radiation.

The adjustment of the x-ray parameters is generally governed by a fixed scheme, which is applied as a basis for regulating the x-ray parameters. Specific requirements for the control behavior, for example a short pulse width for a cardiological application, are merely taken into account by corresponding limit values, such as for example a pulse width of less than 10 ms. This limit value will not be exceeded when the x-ray parameters are changed and the application-specific requirement for the x-ray images is insured, such as for example a high temporal resolution for a cardiological application.

However only a generally valid application-specific adjustment of the pulse width is possible through such fixed limit values, an actual patient-specific situation cannot be taken into account. It is precisely during a cardiological application, in which a high time resolution is briefly not required, that this leads to sub-optimal conditions. For example an increased signal also occurs then on the basis of the usual x-ray parameters, although a longer pulse width would have fully provided an acceptable image quality.

SUMMARY

Embodiments of the invention specify a method, an x-ray imaging device and a digital storage medium for automatic control of the exposure during x-ray imaging.

According to at least one embodiment of the invention, a method, x-ray imaging device and digital storage medium are disclosed. Advantageous developments are disclosed in the claims.

At least one embodiment of the invention is directed to a method for automatically controlling exposure in x-ray imaging of an object that is moving and is to be irradiated, the method comprising:
  creating x-ray images at different points in time with a pulse width of an x-ray radiation;
  establishing at least one moving area of the image from at least two of the x-ray images created;
  establishing at least one moving edge of the at least one moving area of the image;
  selecting at least one pixel of the at least one moving edge;
  establishing a time dependence of an intensity of the at least one pixel selected, from the x-ray images created;
  evaluating the time dependence of the intensity; and
  changing the pulse width as a function of the evaluating.

At least one embodiment of the invention is directed to a method for automatically controlling exposure in x-ray imaging of an object that is moving and is to be irradiated, the method comprising:
  creating x-ray images at different points in time with a pulse width of an x-ray radiation;
  establishing at least one moving area of an image from at least two of the x-ray images created;
  establishing at least one moving edge of the at least one moving area of the image;
  selecting at least one pixel of the at least one moving edge;
  establishing a spatial dependency of an intensity along a path through the at least one pixel from one of the x-ray images created;
  evaluating the spatial dependency of the intensity; and
  changing of the pulse width as a function of the evaluating.

At least one embodiment of the invention is directed to an x-ray imaging device comprising:
  an x-ray emitter;
  an x-ray detector; and
  a processing and control unit, embodied and programmed to automatically control exposure in x-ray imaging of an object that is moving and is to be irradiated, the automatic exposure control including:
    creating x-ray images at different points in time with a pulse width of an x-ray radiation,
    establishing at least one moving area of an image from at least two of the x-ray images created,
    establishing at least one moving edge of the at least one moving area of the image,
    selecting at least one pixel of the at least one moving edge,
    establishing a time dependence of an intensity of the at least one pixel selected, from the x-ray images created,
    evaluating the time dependence of the intensity, and changing the pulse width as a function of the evaluating.

At least one embodiment of the invention is directed to an x-ray imaging device comprising:
an x-ray emitter;
an x-ray detector; and
a processing and control unit, embodied and programmed to automatically control exposure in x-ray imaging of an object that is moving and is to be irradiated, the automatic exposure control including:
creating x-ray images at different points in time with a pulse width of an x-ray radiation,
establishing at least one moving area of an image from at least two of the x-ray images created,
establishing at least one moving edge of the at least one moving area of the image,
selecting at least one pixel of the at least one moving edge,
establishing a spatial dependency of an intensity along a path through the at least one pixel from one of the x-ray images created,
evaluating the spatial dependency of the intensity, and
changing of the pulse width as a function of the evaluating.

At least one embodiment of the invention is directed to an x-ray imaging device with an x-ray emitter and an x-ray detector, for example a C-arm x-ray device, wherein at least one embodiment of the inventive method is carried out in a processing and control unit.

At least one embodiment of the invention is directed to a digital storage medium with control signals that can be read out electronically, which operate in conjunction with the processing and control unit so that at least one embodiment of the inventive method is carried out.

BRIEF DESCRIPTION OF THE DRAWINGS

Further special features and advantages of the invention will become evident from the following explanations of a number of example embodiments based on schematic drawings.

In the figures:

FIG. 1 shows a flow diagram of a method for automatic exposure control with an evaluation of the time dependence of the intensity, FIG. 2 shows a flow diagram of a method for automatic exposure control with an evaluation of the spatial dependency of the intensity and FIG. 3 shows a C-arm x-ray device with an automatic exposure control.

DETAILED DESCRIPTION OF THE EXAMPLE EMBODIMENTS

A more detailed description of a number of example embodiments will follow.

In accordance with at least one embodiment of the invention, the exposure during the x-ray imaging is optimized with an automatic control of the pulse width of the x-ray radiation, wherein the spatial or the temporal intensity dependency of a pixel of a moving edge of a moving area of the image is analyzed. The pulse width is changed as a function of the analysis.

Embodiments of the invention offers the advantage of insuring an optimal image quality and of reducing negative influences of a suboptimal parameter choice, such as for example a loss of contrast caused by a tube voltage that is too high.

At least one embodiment of the invention is directed to a method for automatic exposure control during an x-ray imaging of a moving object to be irradiated. At least one embodiment of the method comprises the following:
1) Creation of x-ray images at different points in time with a predeterminable pulse width of an x-ray radiation,
2) Establishment of at least one moving area of the image from at least two of the created x-ray images,
3) Establishment of at least one moving edge of the moving area of the image,
4) Selection of at least one pixel of the edge,
5) Establishment of the time dependence of the intensity of the pixel from the created x-ray images,
6) Evaluation of the time dependence of the intensity and
7) Changing of the pulse width as a function of the evaluation.

The edge detection is part of a segmentation of elements in the image processing. It attempts to separate planar areas in a digital image from one another, when they are sufficiently distinguished from one another along straight or coursed lines in color or gray value, brightness or texture. Specific edge operators detect the transitions between these areas and mark these as edges.

In a development, the method part 6) can be replaced by the following:
6a) Fourier transformation of the time dependence of the intensity and
6b) Evaluation of the frequency dependency of the Fourier-transformed time dependence of the intensity.

In a further embodiment, a limit frequency can be established in method part 6b) and, in method part 7), the pulse width can be changed as a function of the limit frequency.

In a further embodiment, the limit frequency can be established as 3 dB limit frequency or as 6 dB limit frequency In a further embodiment of the method, the pulse width can be inversely proportional to the limit frequency.

In a development time dependences of the intensity of a number of pixels can be established and an average time dependence can be established from these, wherein with the averaging the subsequent evaluation is undertaken. This enables undesired influences of the image noise to be reduced.

At least one embodiment of the invention is directed to a method for automatic exposure control during an x-ray imaging of a moving object to be irradiated. The method comprises the following:
Creation of x-ray images at different points in time with a predeterminable pulse width of an x-ray radiation,
Establishment of at least one moving area of the image from at least two of the created x-ray images,
Establishment of at least one moving edge of the moving area of the image,
Selection of at least one pixel of the edge,
Establishment of the spatial dependency of the intensity along a path by the pixel from one of the created x-ray images,
Evaluation of the spatial dependency of the intensity,
Changing of the pulse width as a function of the evaluation.

In a development of the method the path can be selected such that it is at right angles to the edge in the image plane.

In a further form of embodiment, the half value width can be established in the evaluation of the spatial dependency and the pulse width can be changed as a function of the half value width.

The half value width of a function with a maximum is the difference between the two argument values, for which the function values have fallen to half the maximum, presumably thus the "width at half height". According in technology the abbreviation FWHM (Full Width at Half Maximum) is also commonly used.

In a further form of embodiment of the method, the pulse width can be indirectly proportional to the half value width.

In a further form of embodiment, spatial dependencies of the intensity of a number of pixels can be established and from these an average spatial dependency can be established, which is used for the further evaluation or analysis. This enables undesired influences of the image noise to be reduced.

At least one embodiment of the invention is directed to an x-ray imaging device with an x-ray emitter and an x-ray detector, for example a C-arm x-ray device, wherein at least one embodiment of the inventive method is carried out in a processing and control unit.

At least one embodiment of the invention is directed to a digital storage medium with control signals that can be read out electronically, which operate in conjunction with the processing and control unit so that at least one embodiment of the inventive method is carried out.

FIG. 1 shows a flow diagram for automatic exposure control in the x-ray imaging of a moving object. The method is characterized by a specific analysis of acquired image data (=x-ray images), of which the result of the evaluation is adequately taken into account within the control of the exposure. This specific analysis is restricted exclusively to the evaluation of the time resolution of the x-ray images, which is essentially influenced by the duration of the x-ray pulse (=pulse width of the x-ray radiation).

To this end, the method step 100, 2D image data of a moving object acquired by an x-ray imaging device is transferred to three software modules of a processing and control unit 1, said modules being as follows:
1. A motion detection module
2. An edge detection module and
3. A profile selection module.

In method step 101 a motion map MM is created with the motion detection module. This motion map MM shows which areas of the image correspond to a movement of the object. The required image evaluation can be undertaken in this case via a partial derivation in the time direction, wherein here the x-ray images with the intensity $I(x,y,t)$ are analyzed.

In method step 102, on the basis of the current x-ray image with the intensity $I(x,y)$ and taking into account the motion map MM, an edge map EM is created in the edge detection module. The edge map EM represents moving edges of the moving object, for example of a vessel. To this end there can be a locally-limited application of an edge detection filter, for example a Sobel operator. In this case only such edges are detected or taken into account as also correspond to a moving image area within the motion map MM.

In accordance with the edge information in the edge map EM, in method step 103, a one-dimensional intensity profile (=absorption profile) is created in the image space with the profile selection module. This profile extends in the time direction t, i.e. it represents the temporal intensity dependency tI of an individual pixel with the intensity $I(x=\text{const.}, y=\text{const.}, t)$. The individual pixel corresponds to a moving edge within the edge map EM.

In method step 104 a one-dimensional intensity dependency tI is transformed in the Fourier space. In this way a kind of temporal MTF (=modulation transfer function) is created.

The Fourier-transformed temporal intensity dependency fI is evaluated in an independent software module in method step 105 in respect of characteristic parameters. For example the 3 dB or 6 dB limit frequency is established. The result of this evaluation is transferred to the exposure control, and is taken into account within the parameter control with a change of the pulse width PW.

FIG. 2 shows a flow diagram of a further method for automatic exposure control in x-ray imaging of a moving object. In method steps 101 to 102, in accordance with the method as described in FIG. 1, an edge map EM is created.

In method step 203, in accordance with the edge information of the edge map EM in the image space, a one-dimensional intensity profile (=absorption profile) is read out. The profile extends however within an individual image PD with the intensity $I(x,y,t=\text{const.})$, i.e. it represents a spatial intensity dependency sI at a fixed point in time along a path. To this end a representative path through the pixel is selected in image PD, so that an adequate evaluation is possible. For example the path is centered at right angles in relation to an edge within the edge map EM.

In the subsequent method step 205 the one-dimensional spatial intensity dependency sI is used directly in order to evaluate specific characteristics. For example the intensity dependency is derived and the half value width is established. The result of the profile evaluation is transferred to the exposure control and is taken into account within the parameter control for changing the pulse width PW.

In a further embodiment of the above methods a number of intensity profiles are created. Through this a number of profiles are created in a Region Of Interest (ROI). The choice of the ROI is likewise based on the edge map EM. The joint evaluation of the profiles is undertaken either independently of one another, wherein the individual results are subsequently combined. For example an average value of the established pulse width is formed. Or there is a combination, for example an averaging, of the different profiles and from this a determination of the pulse width PW.

In a further form of embodiment the methods in accordance with FIG. 1 and FIG. 2 can be combined. For example an average value of the pulse widths PW determined according to the methods is formed.

FIG. 3 shows a C-arm x-ray device with an automatic exposure control. Arranged opposite one another on a C-arm 4 are an x-ray emitter 2 and an x-ray detector 3. The above methods for exposure control are carried out in a processing and control unit 1.

Although the invention has been illustrated and described in greater detail by the example embodiments, the invention is not restricted by the disclosed examples and other variations can be derived therefrom by the person skilled in the art, without departing from the scope of protection of the invention.

LIST OF REFERENCE CHARACTERS

1 Processing and control unit
2 X-ray emitter
3 X-ray detector
4 C-arm
EM Edge map f Frequency
fI Fourier-transformed temporal intensity dependency
I Intensity of a pixel
MM Motion Map
PD Image data or image
sI Spatial intensity dependency
t Time
tI Temporal dependency of the intensity I
x, y Coordinates
100 Acquisition and forwarding of 2D x-ray images
101 Detection of a movement and creation of a motion map MM
102 Detection of moving edges and creation of an edge map EM
103 Creation of a temporal dependency of the intensity I of a pixel
104 Fourier transformation
105 Analysis of the Fourier-transformed temporal intensity dependency fI
203 Creation of a spatial dependency of the intensity I of a pixel of an image
205 Analysis of the spatial intensity dependency sI

The invention claimed is:

1. A method for automatically controlling exposure in x-ray imaging of an object that is moving and is to be irradiated, the method comprising:
creating x-ray images at different points in time with a pulse width of an x-ray radiation;
establishing at least one moving area of an image from at least two of the x-ray images created;
establishing at least one moving edge of the at least one moving area of the image;
selecting at least one pixel of the at least one moving edge;
establishing a time dependence of an intensity of the at least one pixel selected, from the x-ray images created;
evaluating the time dependence of the intensity; and
changing the pulse width as a function of the evaluating.

2. The method of claim 1, wherein the evaluating of the time dependence of the intensity includes:
fourier transforming the time dependence of the intensity; and
evaluating a frequency dependency, of the time dependence of the intensity after being Fourier-transformed.

3. The method of claim 2, wherein
a limit frequency is established in the evaluating of the frequency dependency; and
the changing of the pulse width includes changing the pulse width as a function of the limit frequency established.

4. The method of claim 3, wherein the limit frequency is established as a 3 dB limit frequency or as a 6 dB limit frequency.

5. The method of claim 4, wherein the pulse width is inversely proportional to the limit frequency.

6. The method of claim 3, wherein
the pulse width is inversely proportional to the limit frequency.

7. The method of claim 3, wherein the time dependence of the intensity of each of a number of pixels are established and from the time dependence of the intensity of each of the number of pixels, an average time dependence is established, the average time dependence being used for the evaluating of the time dependence of the intensity.

8. The method of claim 2, wherein the time dependence of the intensity of each of a number of pixels are established and from the time dependence of the intensity of each of the number of pixels, an average time dependence is established, the average time dependence being used for the evaluating of the time dependence of the intensity.

9. The method of claim 1, wherein
the establishing includes establishing a time dependence of the intensity of each of a number of pixels from the time dependence of the intensity of each of the number of pixels, an average time dependence is established, the average time dependence being used for the evaluating of the time dependence of the intensity.

10. A non-transitory digital storage medium storing control signals, able to be read out electronically, to operate in conjunction with a programmable processing and control unit to execute the method of claim 1 when run on the programmable processing and control unit.

11. A method for automatically controlling exposure in x-ray imaging of an object that is moving and is to be irradiated, the method comprising:
creating x-ray images at different points in time with a pulse width of an x-ray radiation;
establishing at least one moving area of an image from at least two of the x-ray images created;
establishing at least one moving edge of the at least one moving area of the image;
selecting at least one pixel of the at least one moving edge;
establishing a spatial dependency of an intensity along a path through the at least one pixel from one of the x-ray images created;
evaluating the spatial dependency of the intensity; and
changing the pulse width as a function of the evaluating.

12. The method of claim 11, wherein the path is selected to be at right angles to the at least one moving edge.

13. The method of claim 12, wherein a half value width is established in the evaluating of the spatial dependency of the intensity and wherein the changing includes changing the pulse width as a function of the half value width.

14. The method of claim 13, wherein the pulse width is indirectly proportional to the half value width.

15. The method of claim 11, wherein a half value width is established in the evaluating of the spatial dependency of the intensity and wherein the changing includes changing the pulse width as a function of the half value width.

16. The method of claim 15, wherein the pulse width is indirectly proportional to the half value width.

17. The method of claim 11, wherein the establishing includes establishing spatial dependencies of intensity of a number of pixels and from the spatial dependencies of intensity of a number of pixels, an average spatial intensity is established, the average spatial intensity being used for the evaluating of the spatial dependency of the intensity.

18. A non-transitory digital storage medium storing control signals, able to be read out electronically, to operate in conjunction with a programmable processing and control unit to execute the method of claim 11 when run on the programmable processing and control unit.

19. An x-ray imaging device comprising:
an x-ray emitter;
an x-ray detector;
and
a processing and control unit, embodied and programmed to automatically control exposure in x-ray imaging of an object that is moving and is to be irradiated, the automatic exposure control including:
creating x-ray images at different points in time with a pulse width of an x-ray radiation, establishing at least one moving area of an image from at least two of the x-ray images created, establishing at least one moving edge of the at least one moving area of the image, selecting at least one pixel of the at least one moving edge, establishing a time dependence of an intensity of the at least one pixel selected, from the x-ray images created, evaluating the time dependence of the intensity, and changing the pulse width as a function of the evaluating.

20. An x-ray imaging device comprising:

an x-ray emitter;

an x-ray detector; and a processing and control unit, embodied and programmed to automatically control exposure in x-ray imaging of an object that is moving and is to be irradiated, the automatic exposure control including:

creating x-ray images at different points in time with a pulse width of an x-ray radiation, establishing at least one moving area of an image from at least two of the x-ray images created, establishing at least one moving edge of the at least one moving area of the image, selecting at least one pixel of the at least one moving edge, establishing a spatial dependency of an intensity along a path through the at least one pixel from one of the x-ray images created, evaluating the spatial dependency of the intensity, and changing the pulse width as a function of the evaluating.

* * * * *